US00PP08078P

United States Patent [19]

Stravers

[11] Patent Number: Plant 8,078

[45] Date of Patent: Dec. 29, 1992

[54] GERBERA PLANT NAMED TERACHA

[75] Inventor: Lambertus J. M. Stravers, Kudelstaart, Netherlands

[73] Assignee: Terra Nigra BV, PA De Kwakel, Netherlands

[21] Appl. No.: 696,599

[22] Filed: May 7, 1991

[30] Foreign Application Priority Data

Nov. 2, 1990 [NL] Netherlands ..... 1170

[51] Int. Cl.[5] ..... A01H 5/00

[52] U.S. Cl. ..... Plt./68.1

[58] Field of Search ..... Plt./68

*Primary Examiner*—James R. Feyrer

*Attorney, Agent, or Firm*—Foley & Lardner

[57] ABSTRACT

A new and distinct cultivar of Gerbera plant named Teracha, characterized by its single type flower and cup shaped flower form; bright pink ray floret color; green disc florets; lilac-pink perianth lobes and small diameter flower head.

1 Drawing Sheet

The present invention comprises a new and distinct cultivar of Gerbera plant, botanically known as *Gerbera jamesonii,* and referred to by the cultivar name Teracha.

Teracha was originated from a hybridization made in a controlled breeding program in De Kwakel, The Netherlands in 1988 under the supervision of the inventor Lambertus J. M. Stravers.

The female parent was a cultivar designated 87.442. The male parent was a cultivar named M88.138. The new cultivar was discovered and selected as one flower plant within the progeny of the stated parentage by the inventor in or about January 1990 in a controlled environment in De Kwakel.

The first asexual reproduction of Teracha was accomplished when vegetative cuttings were taken from the initial selection in April 1990 in a controlled environment in De Kwakel, The Netherlands by a technician working under formulations established and supervised by the inventor. The new cultivar is presently being propagated by cuttings and tissue culture. Horticultural examination of selected units initiated in November 1990 has demonstrated that the combination of characteristics as herein disclosed for Teracha are firmly fixed and are retained through successive generations of asexual reproduction.

Teracha has not been observed under all possible environmental conditions. The phenotype may vary significantly with variations in environment such as temperature, light intensity and day length. The following observations, measurements and comparisons describe plants grown in commercial greenhouses in De Kwakel, The Netherlands under controlled conditions which closely typify those generally used in commercial practice.

The following traits have been repeatedly observed and have been determined to be basic characteristics of Teracha, which in combination provide a new and distinct cultivar:

1. Single type flower and cup shaped flower form.
2. Ray florets are bright pink in color.
3. Green disc florets.
4. Perianth lobe is lilac pink in color.
5. The diameter of the flower head is small, approximately 65 mm.

Of the many commercial cultivars known to the present inventor, certain comparisons can be made with the new cultivar. The new cultivar Teracha has a relatively small flower diameter (approximately 65 mm) and is similar in this characteristic, and also growth habit, to the cultivars Terkapol, Tertala and Terikatir, all cultivars of the present inventor disclosed in pending plant patent applications. However, Terache differs from the other cultivars in flower color and several other characteristics. The flower color of Teracha, a relatively bright pink, is somewhat similar to the flower color of the cultivar Terbomam which, however, is a lighter and less intense pink. A further difference is that Terbomam has a semi-double flowers.

In comparison to the parent cultivars, the female parent 87.442 has a red flower color with purple discs, and a much larger flower diameter (70–79 mm). The male parent M88.138 has semi-double flower form, pink ray florets and green disc florets, and a somewhat larger (65–75 mm) flower diameter.

The accompanying photographic drawing shows typical inflorescence characteristics of Teracha, with the colors being as nearly true as possible with illustrations of this type.

In the following description, color references are made to The Royal Horticultural Society Colour Chart (R.H.S.). The color values were determined at approximately 9:00 a.m. on Feb. 20, 1991 under natural light at De Kwakel, The Netherlands.

Classification:

*Botanical.*—*Gerbera jamesonii* cv Teracha.

*Commercial.*—Gerbera.

Parentage: Seedling from cross of 87.442 and M88.138.

Plant: The plant when fully grown after approximately five (5) months of growth reaches a height of 40 cm, measured from the soil line.

Leaf blade:

*Length.*—Short.

*Width.*—Narrow.

*Blistering (puckering).*—Medium.

*Hairiness on upper side.*—Medium.

*Depth of cuts or incisions.*—Medium in central part of leaf.

*Color.*—Upper surface of leaf 137A, medium green; lower surface 137C.

*Glossiness on upper side.*—Weak.

*Angle at tip.*—Acute.

*Shape at tip.*—Pointed.
*Margin of lobes.*—Serrate.
*Extension of margin.*—Small.
*Petiole length.*—Medium.
*Petiole anthocyanin coloration.*—Present, medium in intensity.

Peduncle:
*Length.*—Long.
*Cross section.*—Round, medium strength and thickness.
*Hairiness.*—Medium.
*Color.*—Medium green.
*Anthocyanin.*—Present at base, medium in intensity, none present at tip.
*Bracts.*—Absent.

Flower head:
*Type.*—Single; cup shaped in form.
*Diameter from edge to edge.*—Approximately 65 mm; varies somewhat depending on season and stage of development.
*Involucre.*—Height: Tall. Diameter: Small. Bracts: Longitudinal axis on inner rows are straight. Anthocyanin: Absent.
*Ray florets.*—Number in outer row: 40-60. Length of floret: Less than 29 mm. Width of floret: 5-9 mm. Shape of floret: Generally elliptical with narrow base; longitudinal folding is strong. Shape of tip: Rounded, angle obtuse, two teeth, shallow in depth. Cross section of floret: Convex. Color distribution on inner side: Uniform. Striation: Absent. Claw spot: Absent. Color on top side: 55A. Color on bottom side: 49C. Color (general tonality from a distance of 3 meters: Relatively bright pink.
*Disc florets.*—Diameter: 10-19 mm. Main color of perianth lobes: Pink. Color (mature and immature): Green.

Reproductive parts:
*Stigma.*—Main color, white.
*Anthers.*—Main color, yellow; anthocyanin coloration absent.
*Pappus.*—Main color, green.
*Style.*—Main color of distal part is white.

Disease resistance: Medium.
Pest resistance: Medium.

I claim:

1. A new and distinct cultivar of Gerbera plant named Teracha, as illustrated and described.

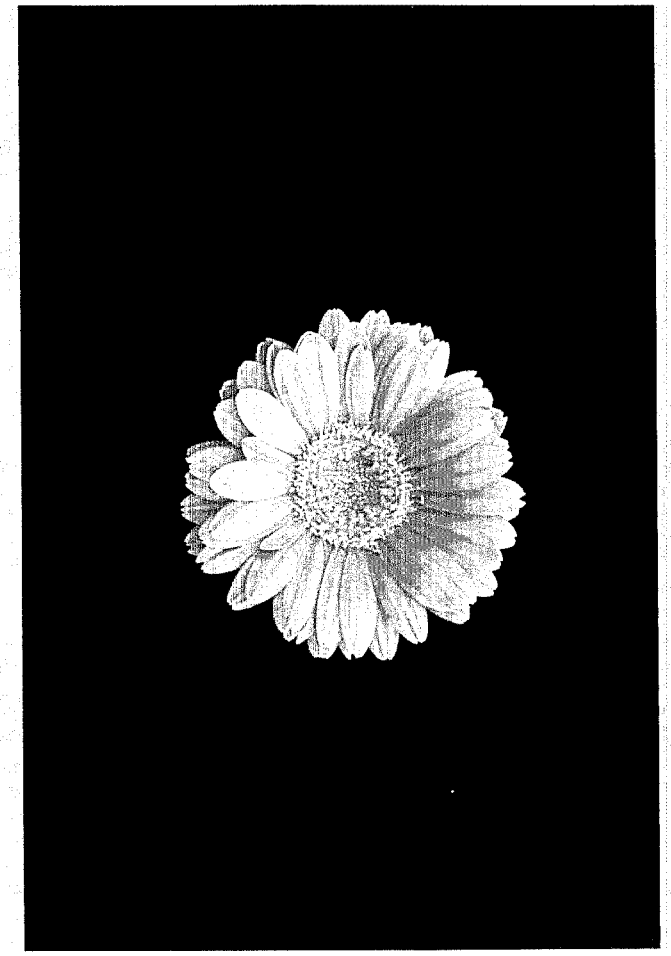

* * * * *